United States Patent [19]

Desai

[11] Patent Number: 5,053,413

[45] Date of Patent: Oct. 1, 1991

[54] N-BENZYLPIPERIDINEISOINDOLINONES

[75] Inventor: Bipinchandra N. Desai, Vernon Hills, Ill.

[73] Assignee: G. D. Searle & Co., Chicago, Ill.

[21] Appl. No.: 402,941

[22] Filed: Sep. 5, 1989

[51] Int. Cl.$^5$ ................. C07D 401/04; A61K 31/445
[52] U.S. Cl. ..................................... 514/323; 546/201
[58] Field of Search ........................ 546/201; 514/323

[56] References Cited

U.S. PATENT DOCUMENTS

| | | |
|---|---|---|
| 3,907,810 | 9/1975 | Caualla et al. ...................... 546/201 |
| 3,910,931 | 10/1975 | Caualla et al. ...................... 546/201 |
| 3,910,932 | 10/1975 | Caualla et al. ...................... 546/201 |
| 3,912,741 | 10/1975 | Caualla et al. ...................... 546/201 |
| 3,917,614 | 11/1975 | Caualla et al. ...................... 546/201 |
| 3,919,242 | 11/1975 | Caualla et al. ...................... 546/201 |
| 4,028,365 | 6/1977 | Caualla et al. ...................... 546/201 |
| 4,029,801 | 6/1977 | Caualla et al. ...................... 546/201 |
| 4,045,444 | 8/1977 | Coualla et al. ...................... 546/201 |
| 4,046,767 | 9/1977 | Caualla et al. ...................... 546/201 |
| 4,061,640 | 12/1977 | Caualla et al. ...................... 546/201 |
| 4,138,492 | 2/1979 | Noverola et al. .................... 546/201 |
| 4,277,501 | 7/1981 | Melley et al. ....................... 546/201 |
| 4,289,781 | 9/1981 | Bengtsson e tal. .................. 546/201 |
| 4,596,827 | 6/1986 | Melley et al. ....................... 546/201 |
| 4,772,617 | 9/1988 | Archibald et al. .................. 546/201 |

FOREIGN PATENT DOCUMENTS 1345872  2/1974  United Kingdom ................ 546/201

OTHER PUBLICATIONS

Fleming, et al., Calcium Channel Agonists/Antagonists (II) (pp. 1564–1565) (1982).

Primary Examiner—Mary C. Lee
Assistant Examiner—Robert C. Whittenbaugh
Attorney, Agent, or Firm—Joy Ann Serauskas; Paul D. Matukaitis

[57] ABSTRACT

N-benzylpiperidineisoindolinones, which have activity as Class III antiarrhythmic agents, acting by prolonging cardiac action potential repolarization. The invention further provides for compositions incorporating the compounds and methods of their use, as well as providing for pharmaceutically acceptable salts of the compounds.

16 Claims, No Drawings

N-BENZYLPIPERIDINEISOINDOLINONES

BACKGROUND OF THE INVENTION

The present invention provides novel compounds, novel compositions, methods of their use and methods of their manufacture, such compounds pharmacologically useful in the treatment of cardiac arrhythmias. More specifically, the compounds of the present invention are Class III antiarrhythmic agents which, by effectively prolonging repolarization of a cardiac cell action potential, can be used effectively to treat certain cardiac arrhythmias.

Antiarrhythmic drugs have been grouped together according to the pattern of electrophysiological effects that they produce and/or their presumed mechanisms of action. Thus, Class I antiarrhythmic agents are characterized by being sodium channel blockers, Class II antiarrhythmic agents are beta-adrenergic blockers, Class III antiarrhythmic agents prolong repolarization, and Class IV antiarrhythmic agents are calcium channel blockers.

Currently, there are very few Class III antiarrhythmic agents available for theraputic use. Among them is bretylium. Bretylium's usefulness is limited, however, and currently its therapeutic use is reserved for life-threatening ventricular arrhythmias that are refractory to other therapy. Thus, bretylium's use is generally confined to intensive care units. It is an object of this invention to provide Class III antiarrhythmic agents of broader theraputic use than existing Class III antiarrhythmic agents.

SUMMARY OF THE INVENTION

The invention relates to novel compounds of the general formula I:

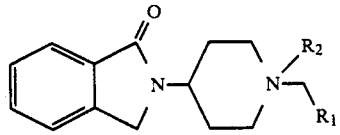

the hydrated forms thereof and the pharmaceutically acceptable salts thereof, wherein $R_1$ is cycloalkyl or aryl, aryl substituted by alkyl of from one to ten carbon atoms, benzodioxole or aryl substituted by alkyloxy of from one to ten carbon atoms; and $R_2$ is an unshared valence bond or alkyl of one to ten carbon atoms.

The compounds and pharmaceutical compositions thereof are useful in the antiarrhythmic methods of the invention. The invention further provides dosage unit forms adapted for oral, topical and parenteral administration. Also provided for in this invention are the pharmaceutically acceptable salts of the compounds.

DETAILED DESCRIPTION OF THE INVENTION

As used herein, the expression "aryl" is defined as phenyl. The term "substituted aryl" shall include phenyl substituted by alkyl of one to ten carbon atoms. The term "alkyloxyaryl" is defined to include alkyl of one to ten carbon atoms and aryl which may be unsubstituted phenyl or phenyl substituted by alkyl of one to ten carbon atoms. The term "alkyl" is defined to include straight or branched carbon-carbon linkages of one to ten carbon atoms. The term "cycloalkyl" is defined to include cyclic alkyl carbon-carbon linkages of five to eight carbon atoms.

The term "benzodioxole" is defined to mean the substituent of the formula

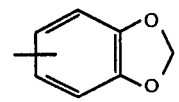

The term "cardiac arrhythmia" is defined to mean any variation from the normal rhythm of the heartbeat, including, without limitation, sinus arrhythmia, premature heartbeat, heartblock, fibrillation, flutter, pulsus alternans, tachycardia, paroxysmal tachycardia and premature ventricular contractions.

The term "repolarization of cardiac cells" is defined as those phases of a cardiac action potential during which time a depolarized cardiac cell is reverting to normal pre-polarization transmembrane voltage.

The term "pharmaceutically acceptable salts" refers to non-toxic salts of the compounds of this invention which are generally prepared by reacting the free base with a suitable organic or inorganic acid. Representative salts include the hydrochloride, hydroiodic, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate and the like salts.

Compounds of the invention can be prepared readily according to the following reaction scheme or modifications thereof using readily available starting materials, reagents and conventional synthesis procedures. In these reactions, it is also possible to make use of variants which are in themselves known, but are not mentioned in greater detail.

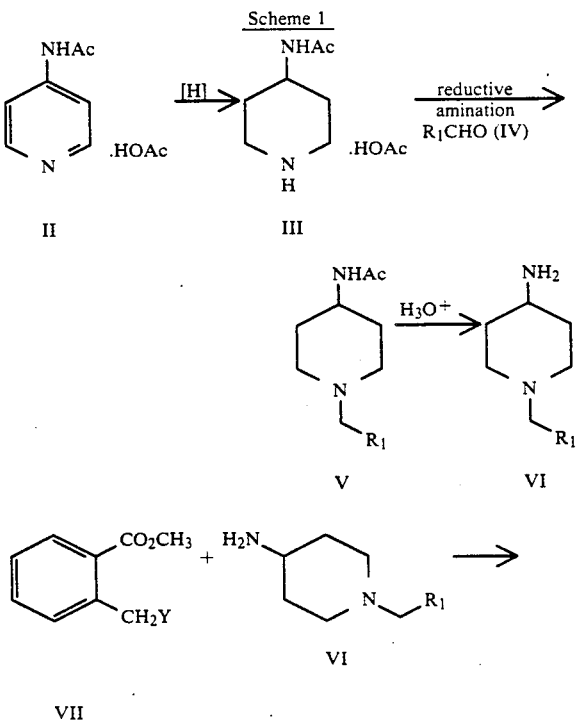

-continued
Scheme 1

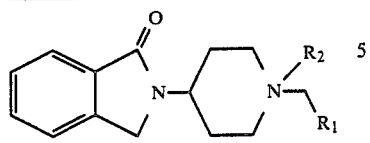

I

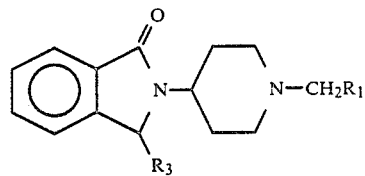

IX

The compounds of this invention may be prepared by a variety of methods. Unless otherwise specified, the various substituents are defined as for formula I above. Y is, for example, a suitable leaving group such as halogen, a tosylate moiety or a mesylate moiety.

Compounds of formula I may be prepared by the methods outlined in U.S. Pat. No. 4,600,758 (Terence M. Dolak and Tellis A. Martin) or U.S. Pat. No. 4,289,781 (Karl S. Bengtsson, Seth O. Thorberg, and Sven O. Ogren). The preferred method is outlined in Scheme 1.

Reduction of 4 acetamidopyridine Formula II affords 4 acetamidopiperidine Formula III. A method for the preparation of 4-acetamidopiperidine III involves the reduction of 4-acylamino N-benzyl pyridinium compounds by alkali metal hydrides or catalytic hydrogenation of the aromatic ring with debenzylation as described in EP 1,537,16 (G. O. Weston) and EP 1,345,872 (J. L. Archibald and J. F. Cavalla). Preferred reduction conditions employ a ruthenium on carbon catalyst in a solvent such as alcohol, THF, or acetic acid under an atmosphere of hydrogen. Subsequent reductive alkylation of the piperidine Formula III with aldehydes Formula IV provides the N-arylmethyl intermediates Formula V. Preferred conditions employ Pt/C catalyst in an inert solvent such as alcohol, THF, or acetic acid under an atmosphere of hydrogen. Alternative preferred conditions employ borane-pyridine complex as the reducing agent at room temperature in alcohol, acetic acid or methylene chloride. Hydrolysis of the amide bond of acetamides Formula V provides amine intermediates Formula VI. Although hydrolysis may be effected in acid or base, the preferred method employs hydrolysis in 1.2 M HCl at 100° C. Phthalimidines I can be prepared by a variety of methods. One method involves reaction of amine VI with a phthalic anhydride to afford the phthalimide Formula VIII which can be reduced with Sn/HCl.

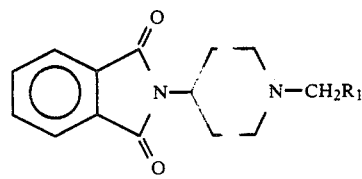

VIII

Another method involves treatment of amines VI with phthalaldehydic acid in the presence of a cyanide salt to give intermediate IX ($R_3$=CN) which can be hydrolyzed to give the carboxylic acid IX ($R_3$=COOH) and decarboxylated by heating at 100–200° C. under dry conditions to give phthalimidines I. A further method involves the reaction of amines VI with phthalide of

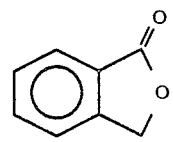

X formula X. A preferred method involves the reaction of amines Formula VI with ortho-toluic ester derivatives Formula VII which bear a suitable leaving group Y (such as halogen, mesylate, or tosylate). The preferred method employs alkyl 2-bromomethyl-benzoates in a refluxing inert solvent such as toluene or chloroform. The phthalimidine intermediates Formula I are subsequently converted to the quaternary salts Formula I (that is, where $R_2$ is not an unshared valence bond) by N-alkylating reagents Formula IX in an inert solvent. Preferred alkylation conditions employ acetonitrile as the solvent at room temperature.

The compounds of the present invention can be administered in such oral dosage forms as tablets, capsules, pills, powders, granules, elixers, tinctures, suspensions, syrups and emulsions. Likewise, it can also be administered in intravenous, intraperitoneal, subcutaneous or intramuscular form, all using forms known to those of ordinary skill in the pharmaceutical arts. In general, the preferred form of administration is oral.

An effective but non-toxic amount of the compound is employed in the treatment of arrhythmias of the heart. The dosage regimen utilizing the compound of the present invention is selected in accordance with a variety of factors including the type, species, age, weight, sex and medical condition of the patient; with the severity of the condition to be treated; the route of administration; the renal and hepatic function of the patient; and the particular compound employed or salt thereof. An ordinarily skilled veterinarian or physician can readily determine and prescribe the effective amount of the drug required to prevent, treat or arrest the progress of the condition.

Oral dosages of the compounds of the present invention, when used for the indicated cardiac effects, will range between about 0.1 mg per kilogram of body weight per day (mg/kg/day) to about 1000 mg/kg/day and preferably 1.0 to 100 mg/kg/day. Advantageously, the compounds of the present invention can be administered in a single daily dose or the total daily dosage can be administered in divided doses of two, three or four times daily.

In the pharmaceutical compositions and methods of the present invention, the compounds described in detail below will form the active ingredient that will typically be administered in admixture with suitable pharmaceutical diluents, excipients or carriers (collectively referred to herein as "carrier" materials) suitably selected with respect to the intended form of administration, that is, oral tablets, capsules. elixers, syrups and the like, and consistent with conventional pharmaceutical practices.

For instance, for oral administration in the form of tablets or capsules, the active drug component can be combined with an oral non toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form, the active drug components can be combined with any oral nontoxic pharmaceutically acceptable inert carrier such as ethanol, glycerol, water, and the like. In the case of oral administration and in liquid form, suitable flavoring carriers can be added such as cherry syrup and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol and various waxes. Lubricants for use in these dosage forms include magnesium stearate, sodium benzoate, sodium acetate, sodium stearate, sodium chloride, sodium oleate and the like. Disintegrators include, without limitation, starch, methycellulose, agar, centonite, xanthan gum and the like.

The compounds of this invention can also be administered by intravenous route in doses ranging from 0.01 to 10 mg/kg/day.

Furthermore, it is also contemplated that the invention can be administered in an intranasal form topically via the use of suitable intranasal vehicles, or via transdermal routes, using those forms of transdermal skin patches well known to those of ordinary skill in that art. In the case of transdermal skin patch administration, daily dosage is continuous via the transdermal delivery system rather than divided, as in an oral delivery system.

The compounds of this invention exhibit antiarrythmic activity useful in the treatment of various cardiac arrhythmias. The test procedures employed to measure this activity of the compounds of the present invention are described below.

Example 1

Guinea pigs, of either sex weighing between 200–350 g, are acutely sacrificed and the right ventricular papillary muscle is isolated. A sample of a given test compound is added using an in vitro tissue bath. Concentrations used are generally $3 \times 10^{-5}$M, but may also be as low as $3 \times 10^{-7}$M. Changes in refractory period are measured before and after adding 1 concentration (usually $3 \times 10^{-5}$M, as noted above) of a test compound to the bath. One hour is allowed for drug equilibration. A compound is considered active (Class III) if an increase in ventricular refractory period is 25 msec or more (at $3 \times 10^{-5}$M).

| Compound | Results Concentration (M) | Change (msec) |
|---|---|---|
| H₂O | — | 8 |
| Disopyramide | $3 \times 10^{-5}$ | 20 |
| Clofilium | $3 \times 10^{-5}$ | 24 |
| Sotalol | $3 \times 10^{-5}$ | 35 |
| Example 6 | $1 \times 10^{-6}$ | 75 |
| Example 7 | $3 \times 10^{-5}$ | 65 |
| Example 8 | $3 \times 10^{-5}$ | 80 |

The following non-limiting examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Melting points were determined on a Thomas Hoover Unimelt (Capillary Apparatus and are not corrected. Unless otherwise noted, I.R. and NMR spectra were consistent with the assigned structure.

EXAMPLE 2

4-acetamidopyridine acetate

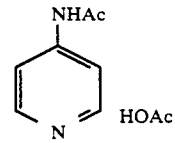

4-Aminopyridine (101.28 g) and acetic anhydride (110 g) were mixed neat and heated at 100° C. for 1/2 h. The solidified reaction mixture was triturated with acetone, filtered off, and washed with ether to afford 186.48 g of title compound as a white solid in two crops.

Anal. calcd for C C, 55.09; H, 6.16; N, 14.26. Found: C, 55.04; H, 5.96; N, 15.22.

EXAMPLE 3

4-acetamidopiperidine acetate

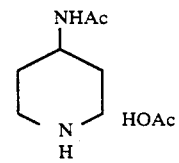

A solution of the product of Example 2 (75 g) in 750 mL acetic acid was reduced over PtO₂ catalyst at 60 psi hydrogen atmosphere at 60° C. for 7 hours. The solution was filtered, concentrated and triturated with ether to afford the title compound quantitatively as a white solid which was used directly in subsequent reactions.

EXAMPLE 4

1 (4-methoxyphenyl)methyl-4-acetamidopiperidine

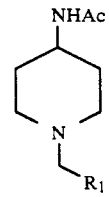

A mixture of 10 g amine acetate, the product of Example 3, and 13.48 g 4 methoxy benzaldehyde was hydrogenated in 100 mL ethanol over a Pt/C catalyst at room temperature for 3 hours. The reaction mixture was filtered and concentrated to give 74.0 g of the acetate salt of title compound as a white solid which was hydrolyzed directly as described in Example 5. (An alternative reductive amination procedure is described in Example 6). Conversion of a sample to the free base using aqueous base and ethyl acetate extraction provided a white solid after solvent evaporation and trituration with ether: mp 140–142° C.; Anal. calcd for $C_{15}H_{22}N_2O_2$: C, 68.67; H, 8.45; N, 10.68. Found: C, 65.26; H, 8.60; N, 10.77.

EXAMPLE 5

1-(4 methoxyphenyl)methyl-4-amino piperidine

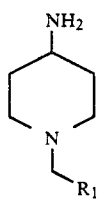

A) A solution of 50 g of the product of Example 4 ($R_1$ = (4-methoxyphenyl)methyl) was dissolved in 500 mL of 1.2 N HCl and heated at 100° C. for 8 h. The solution was made alkaline with 50% aq. NaOH and extracted three times with ether. The combined organic layers were washed with water and saturated brine, dried over sodium sulfate, and concentrated to give the title compound ($R_1$ = (4 methoxyphenyl)methyl) as 28 g of clear oil which was used without further purification.

B) (Alternative general reductive alkylation procedure.) A solution of 50 mmol amine acetate (the product of Example 3) and 100 mmol of 4 methoxybenzaldehyde in 125 mL methylene chloride and 15 mL acetic acid was treated with 50 mmol of borane-pyridine complex and allowed to stir at room temperature overnight. The removal of volatiles by rotary evaporation afforded acetamide (the product of Example 4) ($R_1$ = (4-methoxyphenyl)methyl) as an oil which was dissolved in 300 mL of 1.2 N HCl and heated overnight on a steam bath. The cooled reaction mixture was extracted once with a 50 mL portion of ethyl acetate which was discarded. The aqueous layer was made basic with aq. NaOH and extracted three times with 50 mL ether. The combined layers were washed with water and dried over sodium sulfate. Solvent removal afforded the title compound ($R_1$ = (4-methoxyphenyl)methyl) as a crude oil (yield typically 60–70% for two steps) which was used directly without further purification.

EXAMPLE 6

2-[1[(4-methoxyphenyl)methyl)-4-piperidinyl]-2,3-dihydro-1H-isoindol-1-one

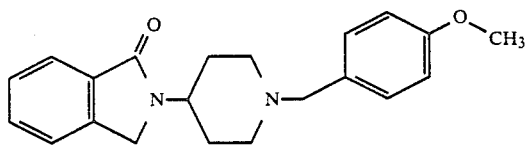

A solution of 2.29 g of methyl 2-bromomethyl benzoate and 2.30 g of amine VI ($R_1$ = (4-methoxyphenyl)methyl) in 25 mL ethanol and 1.4 mL triethylamine were stirred at room temperature for 72 n. The reaction mixture was concentrated and the residue was taken up in 10% HCl and washed twice with ethyl acetate. The ethyl acetate layers were discarded and the acidic solution was made basic with 10% NaOH and extracted thrice with ethyl acetate. The combined organic layers were washed with water and dried over sodium sulfate. Concentration gave 1.05 g of a gum which was recrystallized from ethyl acetate/skellysolve B to give I ($R_1$ = (4-methoxyphenyl)methyl) as 602 mg of white crystalline solid: mp 112–114° C. Anal. calcd for $C_{21}H_{24}N_2O_2$: C, 74.97; H, 7.19; N, 8.32. Found: C, 74.56; H, 7.23; N, 8.22

EXAMPLE 7

2[-1-(phenylmethyl)-4-piperidinyl]-2,3-dihydro-1H-isoindol-1-one

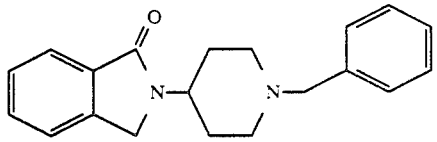

Following the procedure outlined in Example 6 and substituting commercially available 1 phenylmethyl 4-aminopiperidine (2.29 g), 0.60 g of product was isolated as a white crystalline solid from ethyl acetate/skellysolve B: mp 116–118° C. Anal. calcd for $C_{20}H_{22}N_2O \cdot 0.25 H_2O$: C, 77.26; H, 7.29; N, 9.01. Found: C, 77.65; H, 7.38; N, 9.08.

EXAMPLE 8

2-[1-(1,3-benzodioxol-5-ylmethyl)-4-piperidinyl]-2,3-dihydro-1H isoindol-1-one hydrochloride

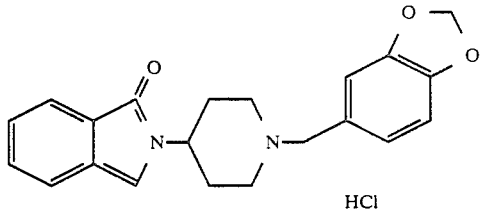

Following the procedure outlined in Example 5 Part B and substituting piperonal for benzaldehyde in the reductive amination reaction afforded amine VI, which was converted to the product I by the procedure described in Example 6; the product was isolated as the hydrochloride salt: mp 253–255° C. (MeOH/ether). Anal. Calcd for $C_{21}H_{22}N_2O_3 \cdot HCl$: C, 65.20; H, 5.99; N, 7.24. Found: C, 64.71; H, 6.04; N, 6.99

EXAMPLE 9

1methyl-4(2,3-dihydro-1-oxo-1H-isoindol-2-yl)-1-(phenylmethyl)piperidinium iodide

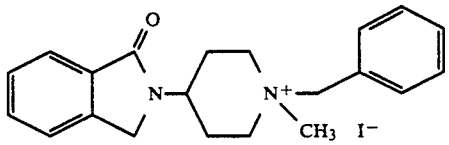

A solution of 2 [-1 (phenylmethyl) 4 piperidinyl]2,3-dihydro-1H isoindol-1-one (I, $R_1$=phenylmethyl. Example 7) was dissolved in 5 mL acetonitrile treated with 0.5 mL of iodomethane. The reaction mixture was allowed to stir for 18 h and the white crystalline precipitate (277 mg) was filtered off to afford I ($R_1$=phenylmethyl, $R_2$=CH$_3$): mp 247-250° C. Anal. calcd for $C_{20}H_{23}IN_2O$: C, 55.31; H, 5.34; N, 6.45. Found: 55.64; H, 5.69; N, 6.52.

While the invention has been described and illustrated with reference to certain preparative embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal being treated for severity of cardiac arrhythmia, dosage-related adverse effects, if any, and analogous considerations. Likewise, the specific pharmacological responses observed may vary according to and depending upon the particular active compounds selected or whether there are present certain pharmaceutical carriers, as well as the type of formulation and mode of administration employed, and such expected variations for differences in the results are contemplated in accordance with the objects and practices of the present invention. It is intended, therefore, that the invention be limited only by the scope of the claims which follow, and that such claims be interpreted as broadly as is reasonable.

What is claimed is:

1. A compound of the formula

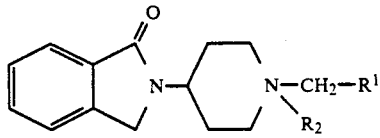

the pharmaceutically acceptable salts thereof, and the hydrated forms thereof, wherein $R^1$ is benzodioxole and $R_2$ is not present or is alkyl of from one to ten carbon atoms, in which case the N of the piperidinyl ring has a plus charge with the proviso that when $R_2$ is alkyl of form one to ten carbon atoms $R^1$ can also be phenyl or phenyl substituted by alkyl of from one to ten carbon atoms.

2. A compound of the formula

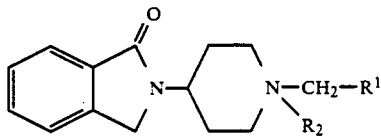

the pharmaceutically acceptable salts thereof, and the hydrated forms thereof, wherein $R^1$ is benzodioxole and $R_2$ is not present or is methyl in which case the N of the piperidine ring has a plus charge with the proviso that when $R_2$ is methyl $R^1$ can also be phenyl.

3. The compound as claimed in claim 2, in which the pharmaceutically acceptable salt is a halogen salt.

4. The compound as claimed in claim 3, in which the halogen is chlorine.

5. The compound as claimed in claim 3, in which the halogen is iodine.

6. A compound as claimed in claim 2, of the formula

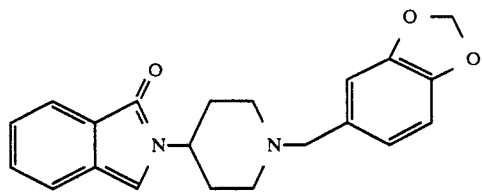

7. A compound as claimed in claim 2, of the formula

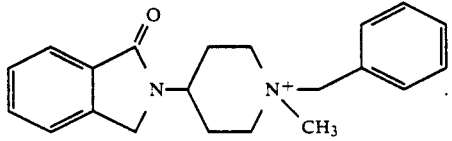

8. A pharmaceutical composition in unit dose form comprised of a pharmaceutically acceptable carrier in combination with a compound according to claim 1 in an amount effective to treat cardiac arrhythmias in an animal or patient to whom one or more unit doses of said composition are administered.

9. The composition as claimed in claim 8, wherein said compound is 2-[1-(1,3-benzodioxol-5-yl methyl)-4-piperidinyl]-2,3-dihydro-1H-isoindol-1-one, monohydrochloride.

10. The composition as claimed in claim 8, wherein said compound is 1-methyl-4-(2,3-dihydro-1-oxo-1H-isoindol-2-yl)-1-(phenylmethyl)piperidinium iodide.

11. A method of regulating cardiac arrhythmias in a mammal comprising administering to such mammal a pharmacologically effective amount of a compound of the formula

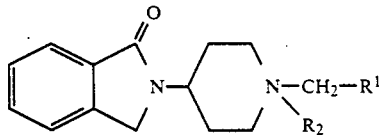

the pharmaceutically acceptable salts thereof, and the hydrated forms thereof, wherein $R_1$ is phenyl, phenyl substituted by alkyl of from one to ten carbon atoms, alkyloxyaryl of from one to ten carbon atoms, or benzodioxole and $R_2$ is not present or is alkyl of from one to ten carbon atoms in which case the N of the piperidinyl ring has a plus charge.

12. A method as claimed in claim 11, wherein said compound is 2-[1-(phenylmethyl)-4-piperidinyl]-2,3-dihydro-1H-isoindol-1-one.

13. A method as claimed in claim 11, wherein said compound is 2-[1-[(4-methyxyphenyl)methyl]-4-piperidinyl]-2,3-dihydro-1H-isoindol-1-one.

14. A method as claimed in claim 11, wherein said compound is 2 [-1 (1,3-benzodioxol-5-yl methyl)-4-piperidinyl]-2,3-dihydro-lH-isoindol-1-one, monohydrochloride.

15. A method as claimed in claim 11, wherein said compound is 1-methyl 4 (2,3-dihydro-oxo lH-isoindol-2-yl)-1-(phenylmethyl) piperidinium iodide.

16. A method of prolonging repolariziation of cardiac cells during a cardiac action potential in a mammal, comprising administering to such mammal of pharmacologically effective amount of a compound of the formula

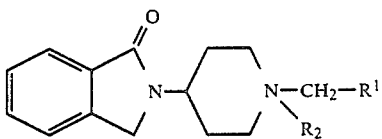

the pharmaceutically acceptable salts thereof, and the hydrated forms thereof, wherein $R_1$ is phenyl, phenyl substituted by alkyl of from one to ten carbon atoms, alkyloxyaryl of from one to ten carbon atoms, or benzodioxole and $R_2$ is not present or is alkyl of from one to ten carbon atoms in which case the N of the piperidinyl ring has a plus charge.

* * * * *

UNITED STATES PATENT AND TRADEMARK OFFICE
CERTIFICATE OF CORRECTION

PATENT NO. : 5,053,413

DATED : October 1, 1991

INVENTOR(S) : Bipinchandra N. Desai

Page 1 of 5

It is certified that error appears in the above-identified patent and that said Letters Patent is hereby corrected as shown below:

Column 1, line 25, reading "theraputic" should read -- therapeutic --

Column 1, line 27, reading "theraputic" should read -- therapeutic --

Column 1, line 32, reading "theraputic" should read -- therapeutic --

Column 3, line 24, reading "4 acetamidopyridine" should read -- 4-acetamidopyridine --

Column 3, line 25, reading "4 acetamidopiperidine" should read -- 4-acetamidopiperidine --

Column 4, line 36, reading "elixers" should read -- elixirs --

Column 5, line 29, reading "centonite," should read -- bentonite, --

Column 5, line 44, reading "antiarryth-" should read -- antiarrhyth- --

Column 6, line 18, reading "(Capillary" should read -- Capillary --

Column 6, line 37, reading "C C," should read -- $C_9H_{12}N_2O_3$: C, --

Column 6, line 59, reading "1 (4-methoxyphenyl)..." should read -- 1-(4-methoxyphenyl)... --

UNITED STATES PATENT AND TRADEMARK OFFICE
CERTIFICATE OF CORRECTION

PATENT NO. : 5,053,413

DATED : October 1, 1991

INVENTOR(S) : Bipinchandra N. Desai

It is certified that error appears in the above-identified patent and that said Letters Patent is hereby corrected as shown below:

Column 7, line 2, reading "4 methoxy benzaldehyde" should read -- 4-methoxybenzaldehyde --

Column 7, line 29, reading "C. for" should read -- C for --

Column 7, line 38, reading "4 methoxybenzaldehyde" should read -- 4-methoxybenzaldehyde --

Column 8, line 2, reading "72 n." should read -- 72 h. --

Column 8, line 35, reading "1 phenylmethyl" should read -- 1-phenylmethyl --

Column 8, line 40, reading "... 0.25 H20:..." should read -- ... 0.25 $H_2O$: ... --

Column 8, line 46, reading "dihydro-1H isoindol-1-one" should read -- dihydro-1H-isoindol-1-one --

Column 9, line 3, reading "1methyl-4(..." should read -- 1-methyl-4(... --

Column 9, line 14, reading "2 [-1 (phenylmethyl) 4 piperidinyl]2,3-" should read -- 2-[-1-(phenylmethyl)-4-piperidinyl]-2,3-

Column 9, line 15, reading "dihydro-1H isoindol-1-one" should read -- dihydro-1H-isoindol-1-one --

UNITED STATES PATENT AND TRADEMARK OFFICE
CERTIFICATE OF CORRECTION

PATENT NO. : 5,053,413            Page 3 of 5
DATED     : October 1, 1991
INVENTOR(S) : Bipinchandra N. Desai It is certified that error appears in the above-identified patent and that said Letters Patent is hereby corrected as shown below:

Column 9, the last structure, reading

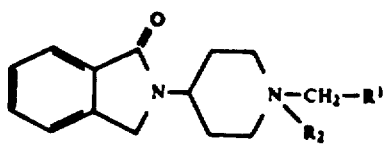    should read    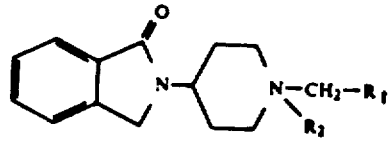

Column 9, line 60, reading "R¹" should read -- $R_1$ --

Column 9, line 65, reading "form" should read -- from --

Column 9, line 65, reading "R¹" should read -- $R_1$ --

Column 10, the first structure, reading

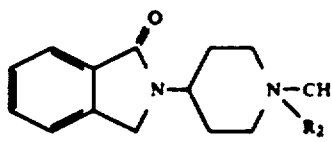    should read    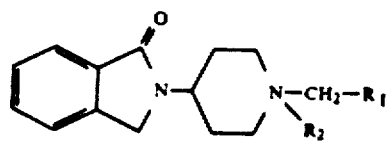

Column 10, line 9, reading "R¹" should read -- $R_1$ --

UNITED STATES PATENT AND TRADEMARK OFFICE
CERTIFICATE OF CORRECTION

PATENT NO. : 5,053,413

DATED : October 1, 1991

INVENTOR(S) : Bipinchandra N. Desai

Page 4 of 5

It is certified that error appears in the above-identified patent and that said Letters Patent is hereby corrected as shown below:

Column 10, line 13, reading "$R^1$" should read -- $R_1$ --

Column 10, the last structure, reading

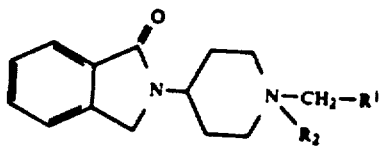   should read   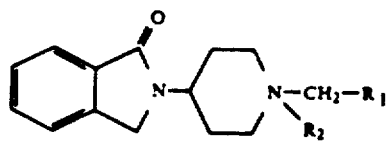

Column 11, line 9, reading "2-[1-[(4-methyxyphenyl)..." should read -- 2-[1-[(4-methoxyphenyl)... --

Column 11, line 12, reading "2 [-1 (1,3-benzodioxol-5-yl" should read -- 2-[1-(1,3-benzodioxol-5-yl --

Column 11, line 16, reading "1-methyl 4 (2,3-dihydro-oxo 1H-isoindol-2-" should read -- 1-methyl-4-(2,3-dihydro-oxo-1H-isoindol-2- --

Column 11, line 18, reading "repoloriziation" should read -- repolarization --

Column 12, line 1, reading "...mammal of pharma-" should read -- ...mammal a pharma- --

UNITED STATES PATENT AND TRADEMARK OFFICE
CERTIFICATE OF CORRECTION

PATENT NO. : 5,053,413
DATED : October 1, 1991
INVENTOR(S) : Bipinchandra N. Desai It is certified that error appears in the above-identified patent and that said Letters Patent is hereby corrected as shown below:

Column 12, the first structure, reading

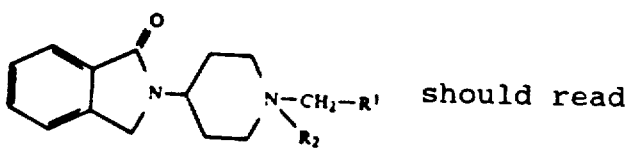 should read 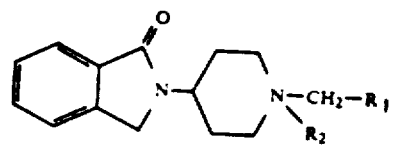

Signed and Sealed this

Seventh Day of December, 1993

Attest:

BRUCE LEHMAN

Attesting Officer    Commissioner of Patents and Trademarks